US010827938B2

(12) United States Patent
Fontanarava et al.

(10) Patent No.: US 10,827,938 B2
(45) Date of Patent: Nov. 10, 2020

(54) SYSTEMS AND METHODS FOR DIGITIZING ELECTROCARDIOGRAMS

(71) Applicant: Cardiologs Technologies SAS, Paris (FR)

(72) Inventors: Julien Fontanarava, Paris (FR); Thomas Bordier, Paris (FR); Jia Li, Paris (FR)

(73) Assignee: Cardiologs Technologies SAS, Paris (FR)

(*) Notice: Subject to any disclaimer, the term of this patent is extended or adjusted under 35 U.S.C. 154(b) by 70 days.

(21) Appl. No.: 16/367,227

(22) Filed: Mar. 27, 2019

(65) Prior Publication Data

US 2019/0298204 A1 Oct. 3, 2019

(30) Foreign Application Priority Data

Mar. 30, 2018 (EP) .................................. EP18305376

(51) Int. Cl.
*A61B 5/04* (2006.01)
*G06N 20/20* (2019.01)
(Continued)

(52) U.S. Cl.
CPC ........ *A61B 5/04012* (2013.01); *A61B 5/7225* (2013.01); *G06K 9/00496* (2013.01);
(Continued)

(58) Field of Classification Search
CPC .. A61B 5/04012; A61B 5/7225; G16H 30/40; G06K 9/6232; G06K 9/00496;
(Continued)

(56) References Cited

U.S. PATENT DOCUMENTS

| 5,024,225 A | 6/1991 | Fang |
| 5,619,991 A | 4/1997 | Sloane |

(Continued)

FOREIGN PATENT DOCUMENTS

| CA | 2466848 A1 | 6/2003 |
| CN | 101268938 A | 9/2008 |

(Continued)

OTHER PUBLICATIONS

Tun et al., Analysis on conversion process from paper record ECG to computer based ECG, MOJ Applied Bionics and Biomechanics, vol. 1 Issue 2-2017, pp. 69-81 (Year: 2017).*

(Continued)

*Primary Examiner* — Said M Elnoubi
(74) *Attorney, Agent, or Firm* — Eversheds Sutherland (US) LLP; Christopher C. Bolten; Robert D. Ward

(57) ABSTRACT

The disclosure relates to systems and methods of converting a representation of a physiological signal (e.g., a non-digitized version such as a printed curve) into a digitized representation of the physiological signal of a subject. For example, a printed electrocardiogram (ECG) may be digitized using the systems are methods provided herein. The method may include receiving a digitized image of a printed curve representing the physiological signal of the subject, and detecting at least one region of interest having a portion of the physiological signal. For each of the regions of interest, the method may include extracting coordinates representing the physiological signal and registering the extracted coordinates.

20 Claims, 9 Drawing Sheets

(51) Int. Cl.
    *A61B 5/00*       (2006.01)
    *G06N 3/04*       (2006.01)
    *G06N 3/08*       (2006.01)
    *G16H 30/40*     (2018.01)
    *G06K 9/62*       (2006.01)
    *G06T 7/12*       (2017.01)
    *G06K 9/00*       (2006.01)

(52) U.S. Cl.
    CPC ......... *G06K 9/6232* (2013.01); *G06N 3/0454* (2013.01); *G06N 3/084* (2013.01); *G06N 20/20* (2019.01); *G06T 7/12* (2017.01); *G16H 30/40* (2018.01); *G06T 2207/20084* (2013.01)

(58) Field of Classification Search
    CPC . G06T 7/12; G06T 2207/20084; G06N 20/20; G06N 3/0454; G06N 3/084
    See application file for complete search history.

(56) References Cited

U.S. PATENT DOCUMENTS

| | | |
|---|---|---|
| 5,819,007 A | 10/1998 | Elghazzawi |
| 5,907,291 A | 5/1999 | Chen et al. |
| 5,966,692 A | 10/1999 | Langer et al. |
| 6,024,699 A | 2/2000 | Surwit et al. |
| 6,157,850 A | 12/2000 | Diab et al. |
| 6,507,753 B1 | 1/2003 | Xue et al. |
| 6,612,985 B2 | 9/2003 | Eiffert et al. |
| 6,656,125 B2 | 12/2003 | Misczynski et al. |
| 6,694,177 B2 | 2/2004 | Eggers et al. |
| 7,142,907 B2 | 11/2006 | Xue et al. |
| 7,289,844 B2 | 10/2007 | Misczynski et al. |
| 7,941,207 B2 | 5/2011 | Korzinov |
| 8,332,017 B2 | 12/2012 | Tarassenko et al. |
| 8,668,644 B2 | 3/2014 | Ong et al. |
| 8,818,496 B2 | 8/2014 | Dziubinski et al. |
| D717,955 S | 11/2014 | Bishay et al. |
| 8,903,479 B2 | 12/2014 | Zoicas |
| 8,932,220 B2 | 1/2015 | Ong et al. |
| 8,951,193 B2 | 2/2015 | Ong et al. |
| D744,659 S | 12/2015 | Bishay et al. |
| 9,241,650 B2 | 1/2016 | Amirim |
| 9,254,095 B2 | 2/2016 | Galloway et al. |
| 9,295,429 B2 | 3/2016 | Ong et al. |
| 9,339,202 B2 | 5/2016 | Brockway et al. |
| 9,345,414 B1 | 5/2016 | Bardy et al. |
| 9,351,652 B2 | 5/2016 | Dziubinski et al. |
| 9,364,155 B2 | 6/2016 | Bardy et al. |
| 9,408,545 B2 | 8/2016 | Felix et al. |
| 9,408,551 B2 | 8/2016 | Bardy et al. |
| 9,420,957 B2 | 8/2016 | Ong et al. |
| D766,447 S | 9/2016 | Bishay et al. |
| 9,433,367 B2 | 9/2016 | Felix et al. |
| 9,433,380 B1 | 9/2016 | Bishay et al. |
| 9,468,386 B2 | 10/2016 | Braojos Lopez et al. |
| 9,504,423 B1 | 11/2016 | Bardy et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,615,763 B2 | 4/2017 | Felix et al. |
| 9,619,660 B1 | 4/2017 | Felix et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,700,227 B2 | 7/2017 | Bishay et al. |
| D793,566 S | 8/2017 | Bishay et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,730,641 B2 | 8/2017 | Felix et al. |
| 9,737,211 B2 | 8/2017 | Bardy et al. |
| 9,737,224 B2 | 8/2017 | Bardy et al. |
| D801,528 S | 10/2017 | Bardy et al. |
| 9,775,536 B2 | 10/2017 | Felix et al. |
| 9,788,722 B2 | 10/2017 | Bardy et al. |
| 9,820,665 B2 | 11/2017 | Felix et al. |
| 9,901,274 B2 | 2/2018 | Bishay et al. |
| 9,936,875 B2 | 4/2018 | Bardy et al. |
| 9,955,885 B2 | 5/2018 | Felix et al. |
| 9,955,888 B2 | 5/2018 | Felix et al. |
| 9,955,911 B2 | 5/2018 | Bardy et al. |
| 10,004,415 B2 | 6/2018 | Bishay et al. |
| 10,045,709 B2 | 8/2018 | Bardy et al. |
| 10,052,022 B2 | 8/2018 | Bardy et al. |
| D831,833 S | 10/2018 | Bishay et al. |
| 10,111,601 B2 | 10/2018 | Bishay et al. |
| 10,123,703 B2 | 11/2018 | Bardy et al. |
| 10,154,793 B2 | 12/2018 | Felix et al. |
| D838,370 S | 1/2019 | Bardy et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,426,364 B2 | 10/2019 | Rapin et al. |
| 2001/0029338 A1 | 10/2001 | Krishnamachari |
| 2004/0147840 A1 | 7/2004 | Duggirala et al. |
| 2004/0230105 A1 | 11/2004 | Geva et al. |
| 2004/0260192 A1 | 12/2004 | Yamamoto |
| 2005/0101873 A1 | 5/2005 | Misczynski et al. |
| 2005/0113706 A1 | 5/2005 | Prystowsky et al. |
| 2005/0171448 A1 | 8/2005 | Korzinov et al. |
| 2005/0182334 A1 | 8/2005 | Korzinov et al. |
| 2005/0222508 A1 | 10/2005 | Moreno et al. |
| 2008/0103403 A1 | 5/2008 | Cohen |
| 2008/0132799 A1 | 6/2008 | Xue |
| 2009/0112110 A1 | 4/2009 | Zhang |
| 2009/0192394 A1 | 7/2009 | Guttag et al. |
| 2010/0268103 A1 | 10/2010 | McNamara et al. |
| 2011/0224565 A1 | 9/2011 | Ong et al. |
| 2011/0257548 A1 | 10/2011 | Dong et al. |
| 2012/0110226 A1 | 5/2012 | Vlach et al. |
| 2013/0116585 A1 | 5/2013 | Bouguerra |
| 2013/0237776 A1 | 9/2013 | Ong et al. |
| 2014/0005998 A1 | 1/2014 | Brockway |
| 2014/0148714 A1 | 5/2014 | Mamaghanian et al. |
| 2014/0187988 A1 | 7/2014 | Ong et al. |
| 2015/0008802 A1 | 1/2015 | Fukuda |
| 2015/0088020 A1 | 3/2015 | Dreisbach et al. |
| 2015/0088024 A1 | 3/2015 | Sackellares et al. |
| 2015/0190067 A1 | 7/2015 | Prystowsky et al. |
| 2015/0257668 A1 | 9/2015 | Braojos Lopez et al. |
| 2015/0282726 A1 | 10/2015 | Grube et al. |
| 2017/0112401 A1 | 4/2017 | Rapin et al. |
| 2017/0238833 A1 | 8/2017 | Felix et al. |
| 2017/0251948 A1 | 9/2017 | Felix et al. |
| 2017/0258358 A1 | 9/2017 | Bishay et al. |
| 2017/0340290 A1 | 11/2017 | Felix et al. |
| 2017/0367609 A1 | 12/2017 | Bardy et al. |
| 2018/0028144 A1 | 2/2018 | Chen et al. |
| 2018/0177423 A1 | 6/2018 | Bishay et al. |
| 2018/0296118 A1 | 10/2018 | Bishay et al. |
| 2018/0310892 A1 | 11/2018 | Perschbacher et al. |
| 2018/0344191 A1 | 12/2018 | Bardy et al. |
| 2018/0353071 A1 | 12/2018 | Bardy et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104961 A1 | 4/2019 | Felix et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |

(56) References Cited

U.S. PATENT DOCUMENTS

| | | | |
|---|---|---|---|
| 2019/0133486 | A1 | 5/2019 | Felix et al. |
| 2020/0015694 | A1 | 1/2020 | Rapin et al. |
| 2020/0022604 | A1 | 1/2020 | Scabellone et al. |

FOREIGN PATENT DOCUMENTS

| | | |
|---|---|---|
| CN | 101766484 A | 7/2010 |
| CN | 102188240 A | 9/2011 |
| CN | 102379694 A | 3/2012 |
| CN | 102779234 A | 11/2012 |
| CN | 103038772 A | 4/2013 |
| CN | 103110417 A | 5/2013 |
| CN | 103284702 A | 9/2013 |
| CN | 103417209 A | 12/2013 |
| CN | 104463326 A | 3/2015 |
| CN | 104970789 A | 10/2015 |
| CN | 106778685 A | 5/2017 |
| DE | 60127354 T2 | 12/2007 |
| EP | 0465241 A2 | 1/1992 |
| EP | 0 465 241 B1 | 11/1998 |
| EP | 1 179 319 A1 | 2/2002 |
| EP | 1 503 664 A2 | 2/2005 |
| EP | 2 030 565 A1 | 3/2009 |
| EP | 2534597 A2 | 12/2012 |
| EP | 3 144 851 A1 | 3/2017 |
| EP | 2 534 597 B1 | 10/2018 |
| JP | 2002172096 A | 6/2002 |
| JP | 2013524865 A | 6/2013 |
| KR | 20150020955 A | 2/2015 |
| WO | WO-03/045224 A2 | 6/2003 |
| WO | WO-03045224 A3 | 11/2004 |
| WO | WO-2006/048881 A2 | 5/2006 |
| WO | WO-2011/115576 A2 | 9/2011 |
| WO | WO-2016/145392 A1 | 9/2016 |
| WO | WO-2017/072250 A1 | 5/2017 |
| WO | WO-2019/038435 A1 | 2/2019 |

OTHER PUBLICATIONS

Kiranyaz, et al., Convolutional Neural Networks for Patient-Specific ECG Classification, 37th Annual International Conference of the IEEE Engineering in Medicine and Biology (EMBC), Aug. 2016, pp. 2608-2611 (Year: 2016).*
Chebil et al., A Novel Method for Digitizing Standard ECG Papers, IEEE Proceedings of the International Conference on Computer and Communication Engineering 2008, pp. 1308-1312 (Year: 2008).*
U.S. Appl. No. 14/924,239, filed Oct. 27, 2015.
U.S. Appl. No. 15/771,807, filed Apr. 27, 2018.
U.S. Appl. No. 16/267,380, filed Feb. 4, 2019.
U.S. Appl. No. 16/328,701, filed Feb. 26, 2019.
International Search Report and Written Opinion dated Aug. 1, 2019 in Int'l PCT Patent Appl. Serial No. PCT/IB2019/052517.
Alfonso et al., "ECG Beat Detection Using Filter Banks", Transactions on Biomedical Engineering, vol. 46, No. 2, Feb. 1999, pp. 192-202, Saint Paul, MN USA.
Almeida et al., "Multilead ECG Delineation Using Spatially Projected Leads From Wavelet Transform Loops", IEEE Transactions on biomedical engineering, vol. 56, No. 8, Aug. 2009, pp. 1996-2005, Zaragoza, Spain.
Badilini et al., ECGScan: A Method for Conversion of Paper Electrocardiographic Printouts to Digital Electrocardiographic Files, Journal of Electrocardiology, 38:310-318 (2005).
Bishop, "Pattern Recognition and Machine Learning", Springer, Information Science and Statistics, 2006, ISBN-10: D-387-31073-8, New York, NY, USA.
Boichat et al., "Wavelet-Based ECG Delineation on a Wearable Embedded Sensor Platform", Proceedings of Wearable and Implantable Body Sensor Networks, 2009, pp. 256-261, Madrid, Spain.
Dr. Dobbs Journal, "Neural Nets and Noise Filtering", p. 32, Jan. 1, 1989.

Chazal et al., "A Patient-Adapting Heartbeat Classifier Using ECG Morphology and Heartbeat Interval Features", IEEE Transactions on Biomedical Engineering, Dec. 2006, vol. 53, No. 12, pp. 2535-2543, Dublin, Ireland.
Chazal et al., "Automatic classification of heartbeats using ECG morphology and heartbeat interval features", IEEE Transactions on Biomedical Engineering, Jul. 2004, vol. 51, No. 7, pp. 1196-1206, Dublin, Ireland.
Chebil et al., A Novel Method for Digitizing Standard ECG Papers, Proceedings of the International Conference on Computer and Communication Engineering 2008, pp. 1308-1312, May 13-15, 2008, Kuala Lumpur, Malaysia.
Choi et al., "Development of ECG beat segmentation method by combining lowpass filter and irregular R—R interval pheckup strategy", Expert Systems with Applications, vol. 37 (2010) pp. 5208-5218, Seoul, Republic of Korea.
Coast et al., "An Approach to Cardiac Arrhythmia Analysis Using Hidden Markov Models", IEEE transactions on biomedical engineering, vol. 37, No. 9, Sep. 1990, pp. 826-836, Pittsburgh, PA, US.
Cybenko, "Approximation by Superpositions of a Sigmoidal Function", Mathematics of Control, Signals and Systems, vol. 2, 1989, pp. 303-314, Urbana, Illinois, USA.
Donahue et al., "Long-term Recurrent Convolutional Networks for Visual Recognition and Description", arXiv:1411.4389v3, pp. 1-13, Feb. 17, 2015, Berkeley, CA, USA.
Dubois et al., "Automatic ECG wave extraction in long-term recordings using Gaussian mesa function models and nonlinear probability estimators", Computer Methods and Programs in Biomedicine, Mar. 2007, vol. 88, pp. 217-233, Pads, France.
EP Search Report and Written Opinion dated Oct. 15, 2018 in EP Patent Appl. Serial No. 18305376.8.
EP Search Report dated Apr. 13, 2016 in European Patent Appl. Serial No. 15191769.7.
Francois Portet, "P wave detector with PP rhythm tracking: Evaluation in different arrhythmia contexts", Physiological Measurement, Institute of Physics: Hybrid Open Access, 2008, 29, pp. 141-155, Scotland, UK.
Fukushima, "Neocognitron: A Self-organizing Neural Network Model for a Mechanism of Pattern Recognition Unaffected by Shift in Position", Biological Cybernetics, vol. 36, 1980, pp. 193-202, Tokyo, Japan.
Hughes et al., "Markov Models for Automated ECG Interval Analysis ", Proceedings of Neural Information Processing Systems, 2004, pp. 611-618, Oxford, UK.
Ieva et al., "Multivariate functional clustering for the morphological analysis of electrocardiograph curves", Journal of the Royal Statistical Society: Series C (Applied Statistics), Blackwell Publishing Ltd, London, UK, 2013, vol. 62, pp. 401-418.
International Search Report & Written Opinion dated Jan. 24, 2017 in Int'l PCT Patent Appl. U.S. Serial No. PCT/EP2016/075972.
International Search Report & Written Opinion dated Nov. 21, 2018 in Int'l PCT Patent Appl. Serial No. PCT/EP2018/072912.
Jin et al., "Deep learning research on clinical electrocardiogram analysis", Science China Press, vol. 45, No. 3, 2015, pp. 398-416, China, English abstract provided.
Johnson et al., "R-Peak Estimation using Multimodal Lead Switching", Computing in Cardiology 2014, pp. 281-284, Oxford, UK.
Kaur et al., "Comparison of different approaches for removal of Baseline wander from ECG signal", Proceedings published by International Journal of Computer Applications, 2011, pp. 30-36, Sangrur (Pb.), India.
Kiranyaz et al, "Real-Time Patient-Specific ECG Classification by 1-D Convolutional Neural Networks", IEEE Transactions on Biomedical Engineering , 63(3):664-675 (2016).
Kiranyaz et al, "Convolutional Neural Networks for Patient-Specific ECG Classification", 37th Annual International Conference of the IEEE Engineering in Medicine and Biology Society (EMBC). Proceedings IEEE Piscataway, N.J., US, Aug. 2015, pp. 2608-2611.
Krizhevsky et al., "ImageNet Classification with Deep Convolutional Neural Networks", Proceedings of Neural Information Processing Systems, 2012, pp. 1097-1105, Toronto, Canada.
Laguna et al., "A Database for Evaluation of Algorithms for Measurement of QT and Other Waveform Intervals in the ECG", Computers in Cardiology, 1997, vol. 24, pp. 673-676, Spain.

(56) References Cited

OTHER PUBLICATIONS

LeCun et al., " Backpropagation Applied to Handwritten Zip Code Recognition", Neural Computation, vol. 1, 1989, pp. 541-551, Holmdel, NJ, USA.

Li et al., "Detection of ECG Characteristic Points Using Wavelet Transforms", Transactions on Biomedical Engineering, vol. 42, No. 1, Jan. 1995, pp. 21-28, Shaanxi, P. R. China.

Li et al., Deep Neural Networks Improve Atrial Fibrillation Detection in Detection in Holter: First Results, European Journal of Preventive Cardiology, European Congress on eCardiology & eHealth, Oct. 2016, Abstract, 23 (2S), 41 (2016).

Lin et al., "Beat-To-beat P And T Wave Delineation in ECG Signals Using a Marginalized Particle Filter", Proceedings of EUSIPCO, Toulouse, France, 5 pages, (2012).

Lin et al., "P and T Wave Delineation and Waveform Estimation in ECG Signals Using a Block Gibbs Sampler", Signal Processing Conference (EUSIPCO), pp. 479-483, Toulouse, France (2012).

Lin et al., "P- and T-Wave Delineation in ECG Signals Using a Bayesian Approach and a Partially Collapsed Gibbs Sampler", IEEE Transactions on Biomedical Engineering, 57(12):2840-2849 (2010).

Long et al., "Fully Convolutional Networks for Semantic Segmentation", Proceedings of Computer Vision and Pattern Recognition, pp. 3431-3440, Berkeley, CA, USA (2015).

Martinez et al., "A Wavelet-Based ECG Delineator: Evaluation on Standard Databases" IEEE transactions on biomedical engineering, vol. 51, No. 4, Apr. 2004, 570-581, Zaragoza, Spain.

Matan et al., "Multi-Digit Recognition Using a Space Displacement Neural Network", Neural Information Processing Systems, Morgan Kaufmann, 1992, pp. 488-495, Holmdel, NJ USA.

Megriche, et al., On the Analysis of a Compound Neural Network for Detecting Atrio Ventricular Heart Block (AVB) in a ECG Signal, International Journal of Medical, Health, Biomedical, Bioengineering and Pharmaceutical Engineering, 2(3):68-78 (2008).

Megriche, et al., on the Analysis of a Compound Neural Network for Detecting Atrio Ventricular Heart Block (AVB) in an ECG Signal, International Journal of Biological and Life Sciences, 4(1):1-11 (2008).

Mnih et al., "Recurrent Models of Visual Attention", Google DeepMind, arXiv:1406.6247v1, pp. 1-12, Jun. 24, 2014.

Noda et al., "Audio-visual speech recognition using deep learning", Appl. Intell., 42:722-737 (2015).

Nowlan et al., "A Convolutional Neural Network Hand Tracker", Advances in Neural Information Processing Systems 7, Morgan Kaufmann, 1995, pp. 901-908, Synaptics, Inc. San Jose, CA USA.

Pan et al., "A Real-Time QRS Detection Algorithm", IEEE Transactions on Biomedical Engineering, vol. BME-32, No. 3, Mar. 1985, pp. 230-236, Shanghai, P.R. of China.

Pigoli et al., "Wavelets in functional data analysis: Estimation of multidimensional curves and their derivatives", Computational Statistics and Data Analysis, vol. 56, 2012, pp. 1482-1498, Politecnico di Milano, Italy.

Prineas et al., "The Minnesota Code Manual of Electrocardiographic Findings", Springer, Second Edition, ISBN D78-1-84882-777-6, 2009, Minneapolis, Minnesota, US.

Ravichandran, et al., Novel Tool for Complete Digitization of Paper Electrocardiography Data, IEEE Journal of Translational Engineering in Health and Medicine, Medical Imaging and Diagnostic Radiology, vol. 1, 7 pages, Jun. 2013.

Rodrigues et al.,"A Neural Network Approach to ECG Denoising", CoRR, Dec. 2012, abs/1212.5217, pp. 1-15, Caparica, Portugal.

Rosenblatt, "The Perceptron: A Probabilistic Model for Information Storage and Organization in the Brain", Psychological Review, vol. 65, No. 6, 1958, pp. 386-408, Buffalo, NY, USA.

Russakovsky et al., "ImageNet Large Scale Visual Recognition Challenge", arXiv:1409.0575v3, pp. 1-43, Jan. 30, 2015, Stanford, CA, USA.

Saini et al., "Automated ECG Delineation using Machine Learning Algorithms", International Congress on Electrocardiology, 2014, pp. 1-4, Jalandhar, India.

Schluter et al., "Improved Musical Onset Detection With Convolutional Neural Networks", IEEE International Conference on Acoustics, Speech, and Signal Processing ICASSP 2014,99 1-5, Linz, Austria.

Shen et al., "Multi-level ECG Classification Based on Independent Component Analysis and Support Vector Machine," Biomedical Engineering and Informatics (BMEI), 2010, vol. 3, pp. 960-964.

Simonyan et al., Very Deep Convolutional Networks for Large-Scale Image Recognition, Published as a conference paper at ICLR, Apr. 10, 2015.

Smith et al., Improved Interpretation of Atrial Dysrhythmias by a New Neural Network Electrocardiogram Interpretation Algorithm, Society for Academic Emergency Medicine, Abstract No. 670, 24(S1):S235 (2017).

Statement of Validation and Accuracy for the Glasgow 12-Lead ECG Analysis Program, Physio Control, Mar. 2009, Redmond, WA USA.

Vaessen, "An approach to ECG Delineation using Wavelet Analysis and Hidden Markov Models", Universiteit Maastricht Institute of Instrument Development Engineering & Evaluation Master Thesis, Sep. 2006.

Zeiler, Matthew D., Adadelta: An Adaptive Learning Rate Method, dated Dec. 22, 2012, prepared while at Google Inc., USA. (arXiv: 1212.5701 [cs.LG].

Zhang et al., "Improving object detection with deep convolutional networks via bayesian optimization and structured prediction", Computer Vision Foundation CVPR2015, pp. 249-258, Zhejiang, China.

Zheng et al., "Time Series Classification Using Multi-Channels Deep Convolutional Neural Networks", Web-Age Information Management, 2014, vol. 8485, pp. 298-310, Switzerland.

International Search Report & Written Opinion dated Jun. 4, 2020 in PCT Patent Appl. Serial No. PCT/IB2020/050850.

* cited by examiner

SYSTEMS AND METHODS FOR DIGITIZING ELECTROCARDIOGRAMS

CROSS-REFERENCE TO RELATED APPLICATIONS

This application claims priority to European Patent Application No. 18305376, filed Mar. 30, 2018, the entire contents of which are incorporated herein by reference.

TECHNICAL FIELD

The present disclosure relates, in general, to the field of physiological signal processing, for example, a method for conversion of a first representation of a physiological signal (e.g., a printed graph) into a digitized representation of the physiological signal of a subject.

BACKGROUND

Electrocardiograms (ECGs) register the electrical activity of the heart by measuring the differences of potential between pairs of electrodes placed on the body. A full electrocardiogram is composed of several signals that correspond to several differences of potential between pairs of electrodes.

While electrocardiographs typically include both printed and digital representations of the recorded electrical activity of the heart, there exists a large database of printed records. A breadth of data may be recovered from these printed records. However, much of this data must be extrapolated from the graphical representation, e.g., relationships between segments of the signal may be evaluated. Such computations and analysis of paper ECGs are tedious and time consuming.

One known approach to retrieving the digital signal from scanned image includes a method which relies on histogram filtering (Ravichandran et al. Novel Tool for Complete Digitization of Paper Electrocardiography Data. *IEEE Journal of Translational Engineering in Health and Medicine*, 1, Jun. 2013. ISSN 2168-2372. doi: 10.1109/JTEHM.2013.2262024). The authors use vertical scanning, after thresholding and median filtering, to identify high-valued pixels corresponding to the signal in the enhanced image. However, these computational steps introduce additional noise on the digitized image.

In view of the foregoing limitations of previously-known systems and methods, a digitization tool for retrieval of the digital signal of a printed ECG and generation of multi-label classifications of the retrieved digital signal and various other metrics and that avoids introduction of additional noise would be desirable.

SUMMARY OF THE INVENTION

Provided herein are systems and methods for converting printed (or analog) ECG data into a digitized curve representing a physiological signal of a subject using machine learning algorithms. A method may include receiving a digitized image of a printed curve representing the physiological signal of a subject and/or any other printed representation of a physiological signal, detecting, via a first neural network, a layout region of the digitized image and at least one sub-region dividing the layout region, detecting, via a second neural network, at least one region of interest inside one of the identified sub-regions having a portion of the physiological signal, and for each region of interest, extracting, via a third neural network, coordinates representing the physiological signal for each of the at least one region of interest, and registering the extracted coordinates.

A method of digital conversion of a printed representation of a physiological signal of a subject may include receiving a digitized image of a printed curve representing the physiological signal of a subject, detecting a layout region of at least one sub-region dividing the layout region, and generating at least one characteristic dimension of the layout region, a position of the layout region, and the number of sub-regions (e.g., using a division neural network). For each of the detected sub-regions, the method may include segmentation of at least one region of interest involving a portion of the physiological signal using a segmentation neural network. The input of the segmentation neural network may be the image of at least one sub-region and the output may be at least one characteristic dimension, dimensions and a position of the at least one region of interest, and/or a probability of the presence of a portion of the physiological signal in the at least one region of interest. For each region of interest, coordinates representing the physiological signal may be extracted using an extraction neural network and registered.

In this manner, the output of the division neural network may be used to define an input for the segmentation neural network and the output of the segmentation neural network may be used to define an input of the extraction neural network. The physiological signal of a subject is an electrocardiogram.

Furthermore, the method may further involve detection of an angle of rotation of the digital image and the generation of a new digital image, wherein the rotation angle is corrected. Also, the detection of a layout region and of at least one sub-region may be realized using a division neural network. The extraction neural network may produce as an output a probability map and the signal may be extracted by calculation of the highest probability.

The one or more of the neural networks may be trained using images of ECG obtained from different ECG devices providing different images formats. The division neural network, the segmentation neural network, and the extraction neural network may be trained separately to achieve the desired outputs described herein.

The division neural network may include at least two hidden layers, the segmentation neural network may include at least two hidden layers, and the extraction neural network may include at least two hidden layers. The division neural network may be a convolutional neural network and include at least two parallel dense layers, one layer corresponding to the output concerning the characteristic dimension of the layout region and one layer corresponding to the number of sub-regions. The segmentation neural network may be a convolutional neural network and include a pooling layer. The extraction neural network may be a convolutional neural network having at least one convolutional layer followed by at least one pooling layer and at least one transpose convolutional layer.

A system of the present disclosure may include instructions stored on at least one processor which may be configured to, when executed, cause the at least one processor to receive a digitized image of a printed curve representing the physiological signal of the subject, and also detect, via a first neural network, a layout region of the digitized image and at least one sub-region dividing the layout region. The instructions may further be configured to, when executed, cause the at least one processor to detect, via a second neural network, at least one region of interest having a portion of the physiological signal inside one of the at least one sub-region, and also extract, via a third neural network, coordinates representing the physiological signal for each of the at least one region of interest.

Another aspect of the disclosure includes a computer program product for the conversion of a digitized curve representing a physiological signal of a subject. The computer program product may include instructions which, when the program is executed by a computer, cause the computer to automatically carry out the steps of the method according to any one of the embodiments described above, wherein the execution of the computer program is activated by a command and said execution is automatic until the output of the digital image.

Another aspect is a computer readable storage medium having instructions which, when the program is executed by a computer, cause the computer to carry out the steps of the method according to any one of the embodiments described above.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
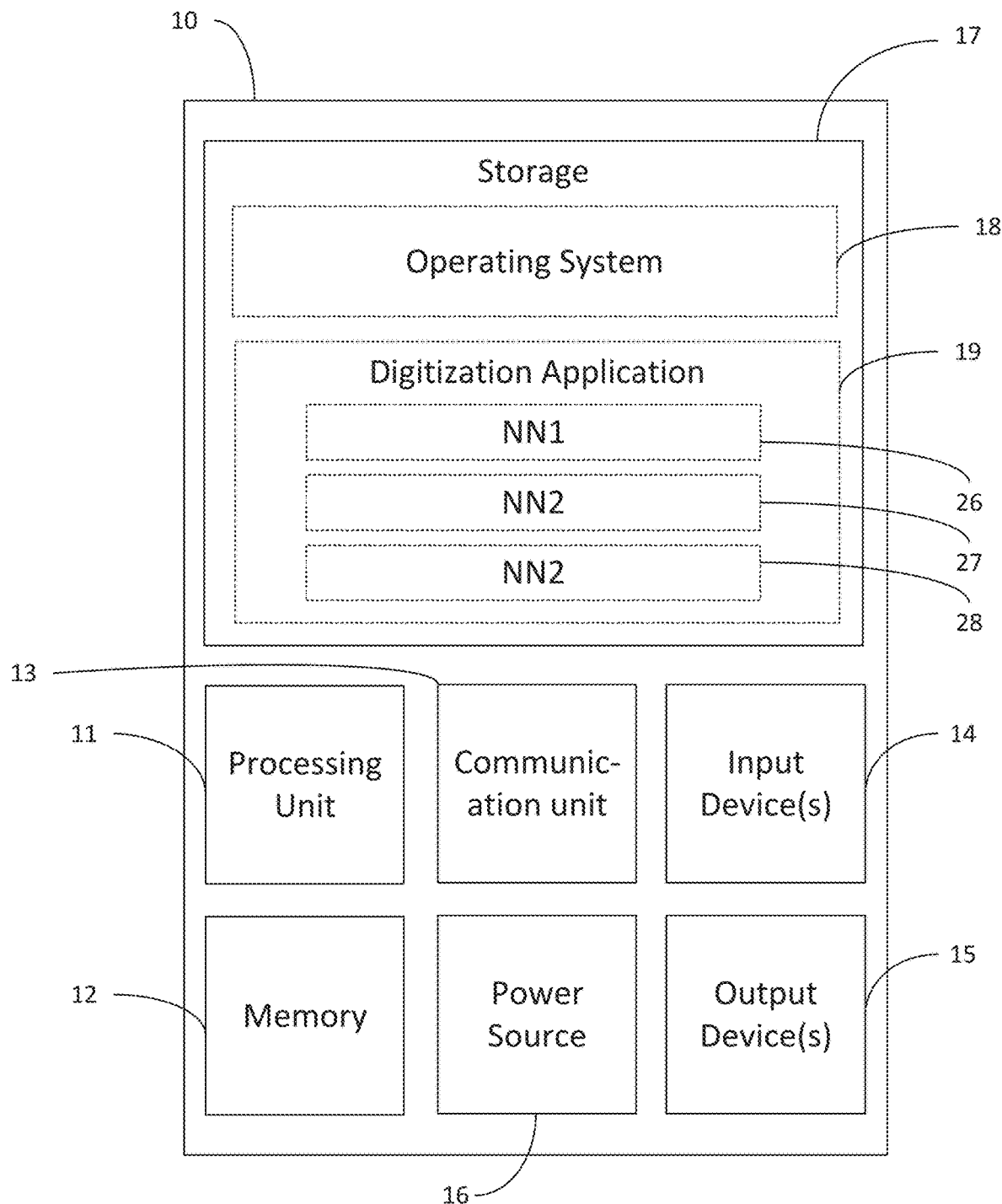
FIG. 1 is a schematic view of exemplary hardware and software components of an exemplary system device.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The following detailed description will be better understood when read in conjunction with the drawings. It should be understood, however, that the application is not limited to the precise arrangements, structures, features, embodiments, and aspect shown. The drawings are not intended to limit the scope of the claims to the embodiments depicted.

In the present disclosure, the following terms may have the following meanings in exemplary embodiments:

"Neural network" may refer to a mathematical structure taking an object as input and producing another object as output through a set of linear and non-linear operations called layers. Such structures may have parameters which may be tuned through a learning phase so as to produce a particular output, and are, for instance, used for classification purposes. The input may then be the object to categorize, and the output may be an estimation of at least a part of the characteristics of the input object. The neural networks described herein may be executed on one or more processors as described in U.S. patent application Ser. No. 16/267,380, filed in Feb. 4, 2019, the entire contents of which are incorporated herein by reference.

"Convolutional neural network" may refer to a neural network which is partly composed of convolutional layers, i.e., layers which apply a convolution on their input.

"Fully convolutional neural network" may refer to a convolutional neural network in which all linear operations are convolutions.

"Convolutional block" may refer to a succession of at least two convolutional layers in a convolutional neural network.

"Weight" may refer to the strength of connections between the nodes. The weights as well as the functions that compute the activation may be modified by a process called learning which is governed by a learning rule.

"Physiological signal" may refer herein to any signal in subjects that may be continually measured and monitored. Physiological signal refers especially to any biological parameter which may be measured by an instrument which converts a physical measure (light, pressure, electricity, radio-signal, etc.) into an analogous signal (in volts).

"Cardiac signal" may refer to the signal recording the electrical conduction in the heart. Said cardiac signal may be for instance an electrocardiogram (ECG) or an endocardiogram. Such signals may have one or more channels, called leads. It may be short term (e.g., 10 seconds in standard ECGs) or long term (e.g., several days in Holters).

"Learning rule" may refer to a method or a mathematical logic which improves the artificial neural network's performance. Usually this rule is applied repeatedly over the network. This improvement is performed by updating the weights and bias levels of an artificial neural network when an artificial neural network is simulated in a specific data environment.

"Stride" may refer to a hyperparameter controlling the output volume of the convolutional layer. More precisely, the stride controls how depth columns around the spatial dimensions (width and height) are allocated. For example, when the stride is equal to 1, the filters move one pixel at a time. This leads to heavily overlapping receptive fields between the columns, and also to large output volumes.

"Subject" may refer to a mammal, e.g., a human. In the present disclosure, a subject may be a patient, e.g., a person receiving medical attention, undergoing or having underwent a medical treatment, or monitored for the development of a disease.

PS—physiological signal;
REC—reception;
$I_d$—digitized image;
$DET_{lr}$—detection of the layout region;
LR—layout region;
SR—sub-regions;
SEG—segmentation of at least one region of interest;
$ROI_s$—region of interest;
$NN_1$—division neural network;
$NN_2$—segmentation neural network;
EXT—extracting coordinates;
$NN_3$—extraction neural network;
REG—registration of the extracted coordinates;
$COOR_{ex}$—extracted coordinates;
DETα—detection an angle (α) of rotation of the digital image.

Referring now to FIG. 1, exemplary functional blocks representing the hardware and software components of system device 10 are shown. Hardware and software components of system device 10 may include one or more processing unit 11, memory 12, storage 17, communication unit 13, and power source 16, input devices 14, and output devices 15. It is understood that system device 10 may be one or more servers in communication with the internet or one or local computing devices.

Processing unit 11 may be one or more processors configured to run operating system 18 and/or digitization application 19. Digitization application 19 running on processing unit 11 may perform the tasks and operations of system device 10 set forth herein. Further, neural networks 26, 27, and 28 may be executed by one or more processors of processing unit 11. Memory 12 may include, but is not limited to, volatile (e.g. random-access memory (RAM)), non-volatile (e.g. read-only memory (ROM)), flash memory, or any combination thereof. Communication unit 13 may receive and/or transmit information to and from other computing devices and peripheral devices (e.g., sensors, cameras, etc.) (not shown). For example, communication unit 13 may permit system 10 to receive a digitized curve and/or image of a physiological signal from a periphery device. Communication unit 13 may be any well-known communication infrastructure facilitating communication over any well-known wired or wireless connection, including over any well-known standard such as any IEEE 802 standard. Power source 16 may be a battery or may connect system device 10 to a wall outlet or any other external source of power. Storage 17 may include, but is not limited to, removable and/or non-removable storage such as, for example, magnetic disks, optical disks, or tape.

Input device 14 may be one or more devices coupled to or incorporated into system device 10 for inputting data to system device 10. Input device 14 may further include a keyboard, a mouse, a pen, a sound input device (e.g., microphone), a touch input device (e.g., touch pad or touch screen), and/or a camera, for example. Output device 15 may be any device coupled to or incorporated into system device 10 for outputting or otherwise displaying data (e.g., display, speakers, printer, etc.).

Digitization application 19 may be stored in storage 17 and executed on processing unit 11. Digitization application 19 may be a software application and/or software modules having one or more sets of instructions suitable for performing the operations of system device 10 set forth herein, including, for example, running one or more neural networks 26, 27 and 28. Neural networks 26, 27, and 28 are also referred to herein as division neural network $NN_1$ 26, segmentation neural network $NN_2$ 27, and extraction neural network $NN_3$ 288.

System device 10 may optionally run operating system 18 stored in storage 17 and executed on processing unit 11. Operating system 18 may be suitable for controlling the general operation of system device 10 and may work in concert with digitization application 19 to achieve the functionality of system device 10 described herein. System device 10 may also optionally run a graphics library, other operating systems, and/or any other application programs. It of course is understood that system device 10 may include additional or fewer components than those illustrated in FIG. 1 and may include more than one of each type of component.

Figure 2:
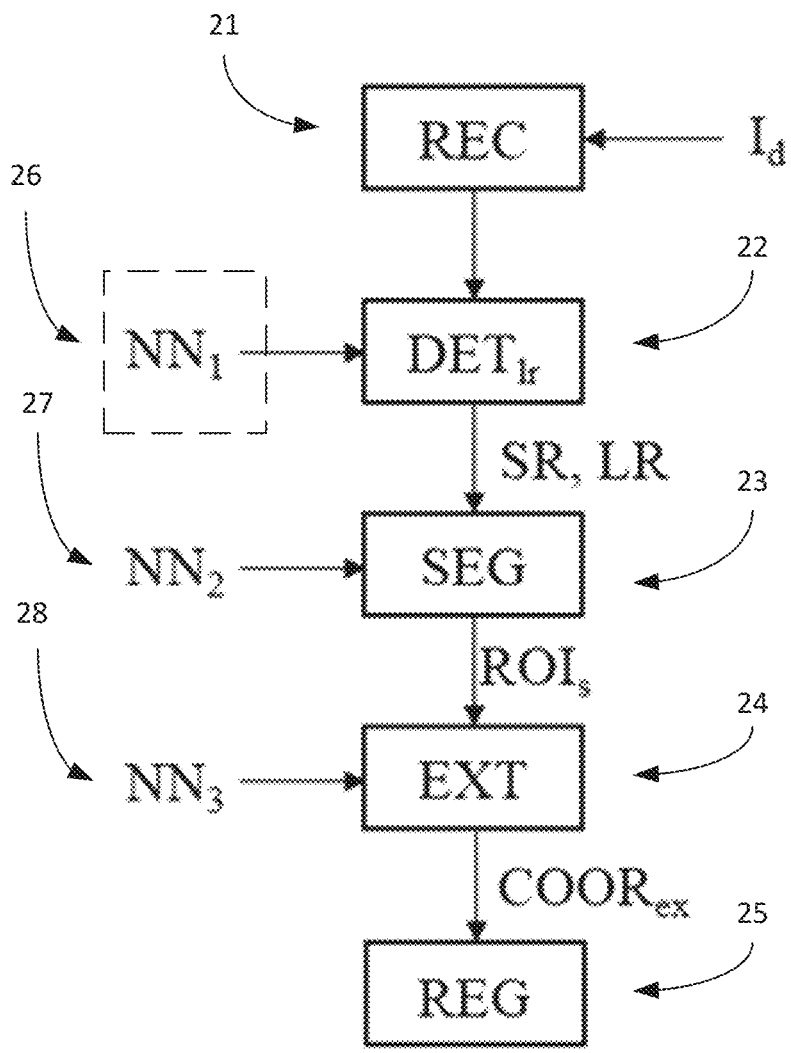
FIG. 2 is a block diagram representing an exemplary method for the conversion of a digitized curve representing a physiological signal of a subject.

Referring now to FIG. 2, a block diagram is illustrated representing the method for the conversion of a digitized curve representing a physiological signal of a subject, according to an aspect of the present disclosure.

The digitized curve may represent a physiological signal of a subject. The digitized curve may be a digitized image $I_d$ of a printed curve representing the physiological signal PS of a subject. The printed curve representing the physiological signal PS may be digitized through means of an image scanner device or a camera comprised in devices like cell phones, tablets and the like.

As is shown in FIG. 2, an image of the curve is received REC at step 21 of FIG. 2. As explained above, the curve of a physiological signal PS of a subject may be an electrocardiogram (ECG). For example, a digitized ECG may be an electrocardiographic signal of variable duration (e.g., from about 1 to about 10 seconds) and a variable number of leads, corresponding to the different directions on which the voltage is recorded.

ECG printed on paper sheets are typically formatted according to a predefined layout. When the electrocardiogram is acquired with 12 leads they may be displayed in different ways, such as for example the more common: 2×6 layout: 6 rows on each of which 2 signals are displayed one after the other. For example, the first 5 seconds come from the first signal's recording, and the last 5 seconds come from the second signal's recording; 3×4 layout: in this layout, there are 4 signals per row, each spanning about 2.5 seconds (see FIG. 4 for an example).

In these predefined layouts, one or more rows may be added at the bottom of the sheet. These rows may be called "rhythm leads": on each of these rows, only one signal is displayed (e.g., spanning 10 seconds). Their purpose is to enable the reader to follow the rhythm and to provide a reference for the reading of other leads.

Alternatively, the physiological signal PS may be an electroencephalographic signal acquired from a plurality of electrodes, an electromyographic signal or any kind of signal representing a physiological electrical activity. The physiological signal PS also may be a multimodal signal.

Figure 3:
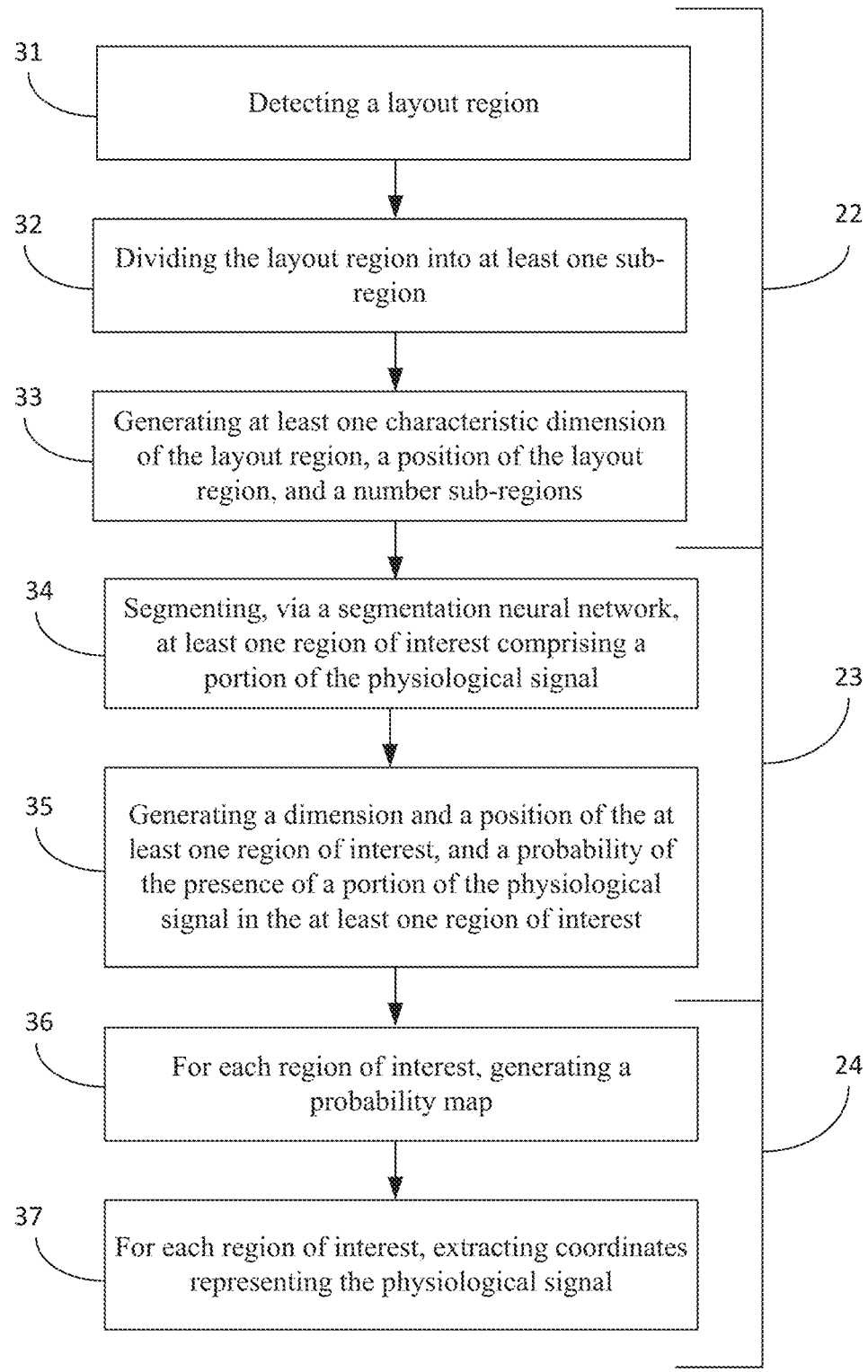
FIG. 3 is a flow chart representing a more detailed view of a portion of the method of FIG. 2.
Figure 4:
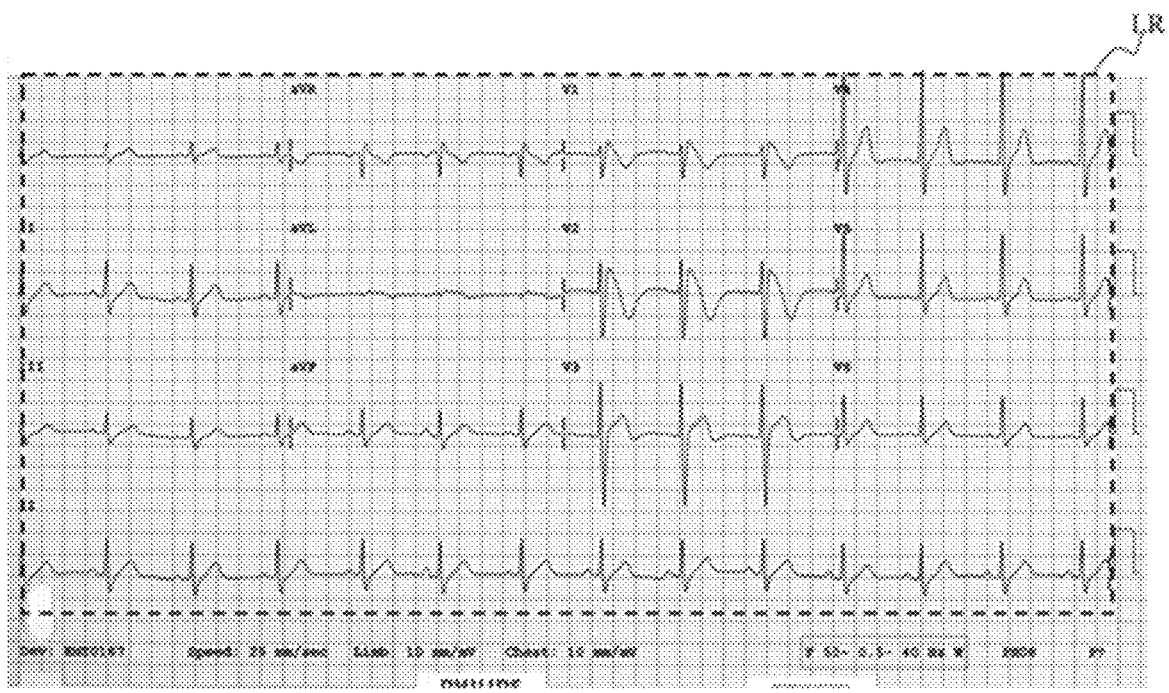
FIG. 4 is an example of a layout region selection for an electrocardiogram representation having 3 rows, 4 columns and 1 rhythm lead (fourth row, from the top to the bottom).

The approach shown in FIG. 2 may include a second step involving detection at step 22. Referring now to FIG. 3, a flow chart of a more detailed view of step 22 is shown. More specifically at sub-step 31, a layout region LR is detected. The layout region LR, which is shown in FIG. 4, is a boundary box sized to capture the physiological signal PS in the image. In an example where the physiological signal PS is an electrocardiogram in a 3×6 layout, the layout region LR is defined by a box with a width and a height, and the position of its center on the image is set so that the 12 leads arranged in the 6 lines and 2 columns plus the rhythm leads are completely encompassed by the box.

Figure 5:
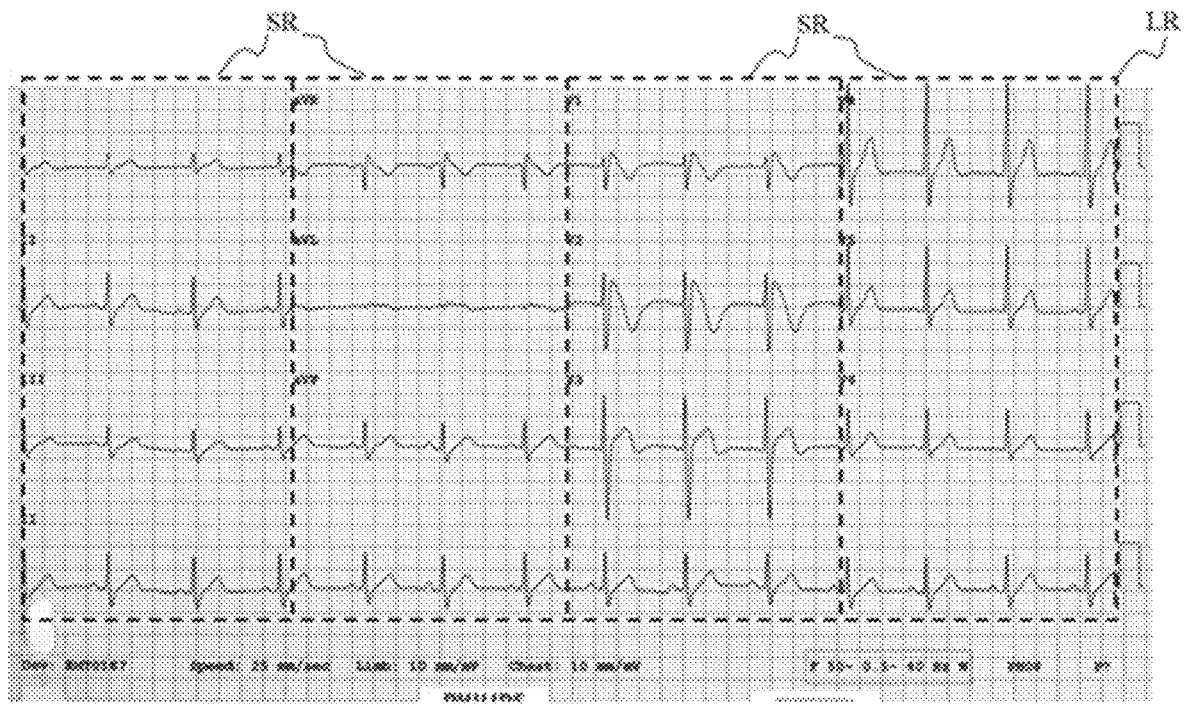
FIG. 5 is an example of multiple sub-regions selected for an electrocardiogram representation having 3 rows, 4 columns and 1 rhythm lead. In this example, 4 rectangular sub-regions are selected.

As is shown in FIG. 3, step 22 may further involve detection of at least one sub-region SR, at sub-step 32, dividing the layout region LR into at least one sub-region. Sub-regions SR, as shown in FIG. 5, are defined by at least one vertical line dividing at least two signal segments. In one example, at least two sub-regions SR are defined by one vertical line as two columns. These steps may be implemented through the use of a graphical interface and the interaction of a user with the interface. The user may use a cursor to interact with the graphical interface and define the layout region LR and the sub-regions SR.

Step 22 may also involve, at sub-step 33, generating at least one characteristic dimension, a position of the layout region LR, and the number of sub-regions SR. The characteristic dimension may be the minimum number of geometrical parameters that define the surface of a geometrical bi-dimensional closed shape (e.g., for a circle, the radius is the characteristic dimension). In one example, the characteristic dimension of the layout region LR is the abscissa and ordinate, in the reference system of the digitized image, for two points defining a diagonal of the boundary box. In this example, the position of the layout region LR is the position of the center of the boundary box. In FIG. 5, the number of sub-regions SR is equal to 2. The detection of the layout region LR and of the sub-regions SR dividing the layout region LR may alternatively be performed in a single step.

The at least one characteristic dimension, a position of the layout region LR, and at least the number of sub-regions SR may be an output from a machine learning algorithm. The machine learning algorithm may implement one of the following learning systems: supervised learning, semi-supervised learning, active learning reinforcement learning or unsupervised learning. The detection DETir of the layout region LR and the sub-regions SR at step 22 may optionally be performed with an algorithm implementing division neural network $NN_1$ 26. In this description, this neural network will be called division neural network or first neural network interchangeably.

An artificial neural network may be a network of simple elements called neurons. These neurons receive an input, change their internal state (activation) according to said input, and produce an output depending on the input and the activation. The network is formed by connecting the output of certain neurons to the input of other neurons in a forward directed graph. The weights as well as the functions that compute the activation may be modified by a process called learning which is governed by a learning rule.

As is shown in FIG. 2, division neural network $NN_1$ 26 may be configured (1) to receive as input a digitized image $I_d$ of a printed curve representing the physiological signal PS of a subject and (2) to generate as output information that may include (i) at least one characteristic dimension, (ii) a position of the layout region LR, and (iii) the number of sub-regions SR (see FIGS. 4 and 5).

Figure 8:
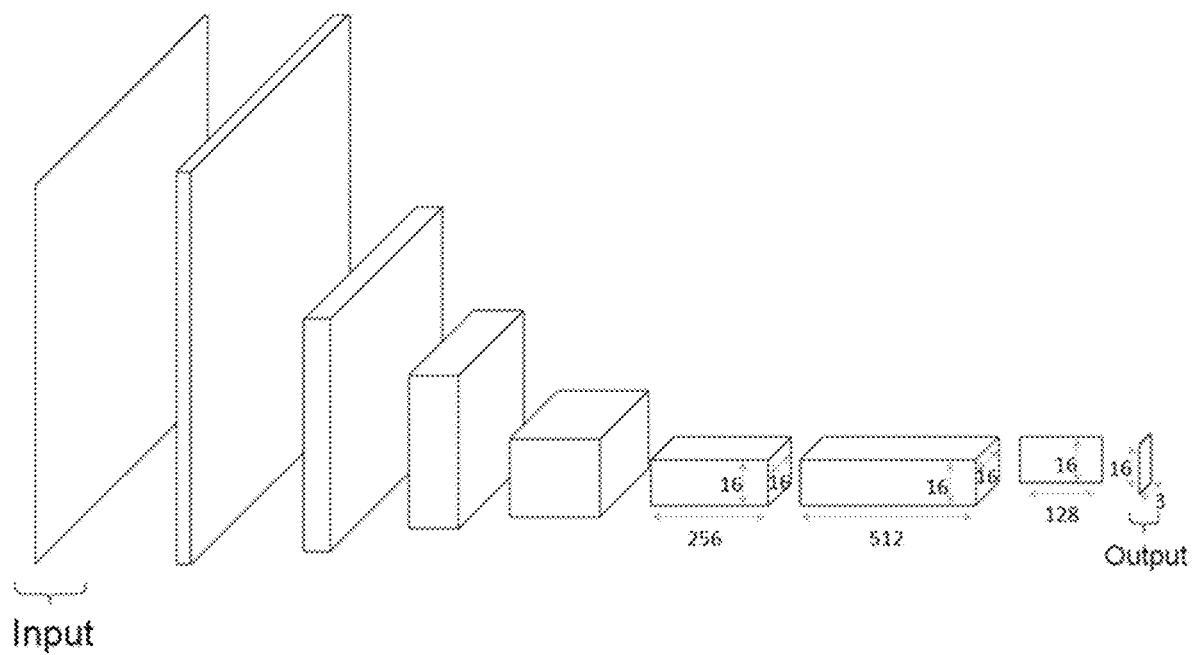
FIG. 8 is an exemplary illustration of architecture of the segmentation neural network.

Division neural network $NN_1$ 26 may be a convolutional neural network. Convolutional neural networks are a particular type of neural network, where one or more of the matrices $W_i$, which are learned, do not encode a full linear combination of the input elements, but the same local linear combination at all the elements of a structured signal such as for example an image or, in this specific context, a cardiac signal, through a convolution (see Fukushima, *Biol. Cybernetics*, Vol. 36, 1980, pp. 193-202 and LeCun et al., *Neural Computation*, Vol. 1, 1989, pp. 541-551). A graphical representation of a convolutional neural network is shown in FIG. 8. Each convolutional neuron processes data only for its receptive field.

Convolutional neural networks allow the network to be deeper with fewer parameters and resolves the vanishing or exploding gradients problem in training traditional multi-layer neural networks with many layers by using backpropagation. The layers of a convolutional neural network have neurons arranged in three dimensions: width, height, and depth. Convolutional neural networks are more adaptable to, for example, image processing that is dominated by spatially local input patterns. Furthermore, a convolutional neural network is shift invariant which makes it fit for image processing.

The image may be preprocessed in a preliminary step. Preprocessing may include any operation known by a skilled artisan such as histogram equalization, filtering, image padding and the like. The preprocessing step may include an operation of re-binning of the image pixels. The re-binning to obtain a smaller image (i.e., a smaller number of pixel) has the advantage of reduction in the calculation time for the subsequent processing steps.

The preprocessing phase may include a step of detecting an angle $\alpha$ of rotation DETa of the digital image $I_d$ and the generation of a new digital image where the rotation angle is corrected.

Division neural network $NN_1$ 26 architecture may be configured to receive as input an image of dimensions (m×n, 1) or (m×n, 3) for color images, where m and n ranges from 28 to 2000 pixels. Division neural network $NN_1$ 26 architecture may be configured to receive as input an image represented in any color model such as RGB, HVS, CMYK and the like. Division neural network $NN_1$ 26 may include multiple hidden layers such as convolutional layers, pooling layers, fully connected layers and normalization layers.

Division neural network $NN_1$ 26 may be composed of convolutional blocks having a number of convolutional layers that ranges from 3 to 30. The advantage of using a convolutional block at the beginning of the division neural network $NN_1$ 26 is to reduce the number of parameters which need to be trained.

The convolutional layers may have a filter with a receptive field of size of (m×n), where m and n are between 3 and 128. The filter size parameters m and n may be inclusively between 3 and 11 to reduce calculation time.

Division neural network $NN_1$ 26 may include a pooling layer, where the pooling is a form of non-linear down-sampling. There are several non-linear functions that may be used to implement pooling, among which max pooling is the most common. The advantage of using pooling layer include progressively reducing the spatial size of the representation, reducing the number of parameters and the amount of computation in the network, and also controlling overfitting. Furthermore, the pooling operation provides another form of translation invariance.

Figure 7:
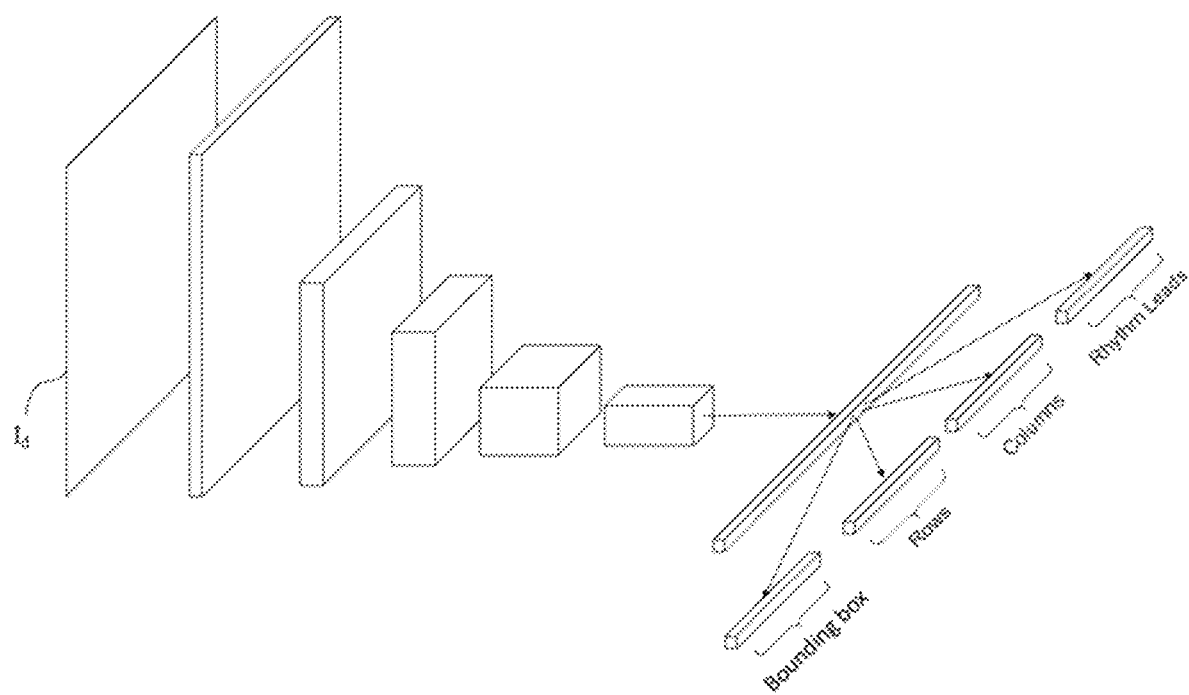
FIG. 7 is an exemplary illustration of architecture of the division neural network.

Referring now to FIG. 7, an exemplary division neural network $NN_1$ 26 is illustrated having five convolutional layers with a filter size of 3×3, each followed by a max pooling layer. Alternation of the convolutional layers and the max pooling layers may be followed by a number of parallel dense layers inclusively between 1 and 10. Division neural network $NN_1$ 26 may include at least one dense layer at the top of the convolution block.

In one example, division neural network $NN_1$ 26 includes, before the alternation of convolutional layers and max pooling layers, a dense layer, followed by 2 parallel dense layers. One parallel dense layer predicts the coordinates (x1; y1; x2; y2) of the boundary box. The other parallel dense layer predicts the number of sub-regions SR.

Division neural network $NN_1$ 26 may be configured to generate as additional output the number of rows on which the leads and/or at least one characteristic dimension and the position of the rhythm lead are arranged. For example, division neural network $NN_1$ 26 involves, at the top of this convolutional block, a one dense layer, followed by 4 parallel dense layers. The parallel dense layer may predict the coordinates (x1; y1; x2; y2) of the boundary box. The other three parallel dense layer may predict the number of sub-regions SR, the number of rows on which the leads are arranged, at least one characteristic dimension, and the position of the rhythm lead.

The parallel dense layers may each be followed by a softmax activation layer to predict a categorical output of the form: $(p_i)$ $i \in N_{categories}$ where $p_i$ are probabilities summing to 1. In one example where the physiological signal PS is an electrocardiogram in a 3×4 layout, $N_{categories}$ is equal to 4 as it is the number of columns and therefore i ranges inclusively between 1 and 4.

Division neural network $NN_1$ 26 may be trained with a supervised training. Loss functions have an important part in artificial neural networks. A loss (regression) function may be used in the training process for the output concerning the layout region LR estimation. A loss function measures the quality of a particular set of parameters based on how well the induced scores agreed with the ground truth labels in the training data. It is a non-negative value, where the robustness of neural network model increases as the value of loss function decreases. The loss function may be a mean square error, mean square logarithmic error, mean absolute error, mean absolute percentage error, L2 or of the like.

In one example, wherein the dimensions and the position of the layout region LR are expressed by the four coordinates $(y_i)$ for $i \in [1,4]$ of the corners of the layout region boundary box, the regression loss is a smooth L1 loss according to the following formula:

$$L(\hat{y}, y) = \sum_{i=1}^{4} smooth_{L1}(\hat{y}_i - y_i)$$

where y and $\hat{y}$ represent the prediction and the true values for the four coordinates of the layout region LR:

$$smooth_{L1}(x) = \begin{cases} 0.5x^2 & \text{if } |x| < 1 \\ |x| & \text{otherwise} \end{cases}$$

A loss function for classification may be used in the training process for the output concerning the number of sub-regions SR. In machine learning and mathematical optimization, loss functions for classification are computationally feasible loss functions representing the price paid for inaccuracy of predictions in classification problems. The loss function for classification used may be a mean square error loss, square loss, hinge loss, logistic loss, cross-entropy loss or any other loss functions for classification known by one skilled in the art.

The loss function for classification may be, for example, categorical cross-entropy, defined as follows:

$$Error(\hat{p}, p) = -\sum_{i=0}^{N_{categories}} p_i \log(\hat{p}_i) = -\log(\hat{p}_k)$$

where p is the target probability, k is the expected category, and $\hat{p}$ is the predicted probability.

Division neural network $NN_1$ 26 may be optimized. Optimization includes the process of finding the set of parameters that minimize the loss function. The division neural network $NN_1$ 26 may be optimized using a gradient descent algorithm.

The optimization step may be performed using ADA-GRAD, ADAM, ADAMAX or SGD (Stochastic Gradient Descent). Other optimization algorithms known by one skilled in the art may be used to implement said optimization step.

An ADADELTA optimizer may be used for division neural network $NN_1$ 26 optimization (Matthew D. Zeiler. "*ADADELTA: An Adaptive Learning Rate Method.*" arXiv: 1212.5701 [cs], December 2012.). The ADADELTA optimizer ensures a robust adaptive learning rate without tuning of a general learning rate (as opposed to Stochastic Gradient Descent) and has been showed to have a more stable learning curve than ADAGRAD.

Division neural network $NN_1$ 26 may be trained using digitized images of ECG obtained from different ECG devices according to different formats. Division neural network $NN_1$ 26 may be trained on a number of training images ranging from about 2 to about 1,000,000. In order to perform a supervised training of division neural network $NN_1$ 26, each of the training image may be associated to annotations concerning the true layout region dimensions and position and the true number of sub-regions.

The output produced by division neural network $NN_1$ 26 may be used to obtain an image of each sub-region SR identified in the digitized image of the physiological signal PS. As is shown in FIG. 2, the output of division neural network $NN_1$ 26 may be used directly as input for segmentation neural network $NN_2$ 27. Alternatively, the output of division neural network $NN_1$ 26 may be used to derive an input for segmentation neural network $NN_2$ 27. In the case of ECG digitization, the sub-region images defined with the output of the division neural network $NN_1$ 26 may be the images associated to the columns of the ECG representation, each of the columns having multiple rows.

Figure 6:
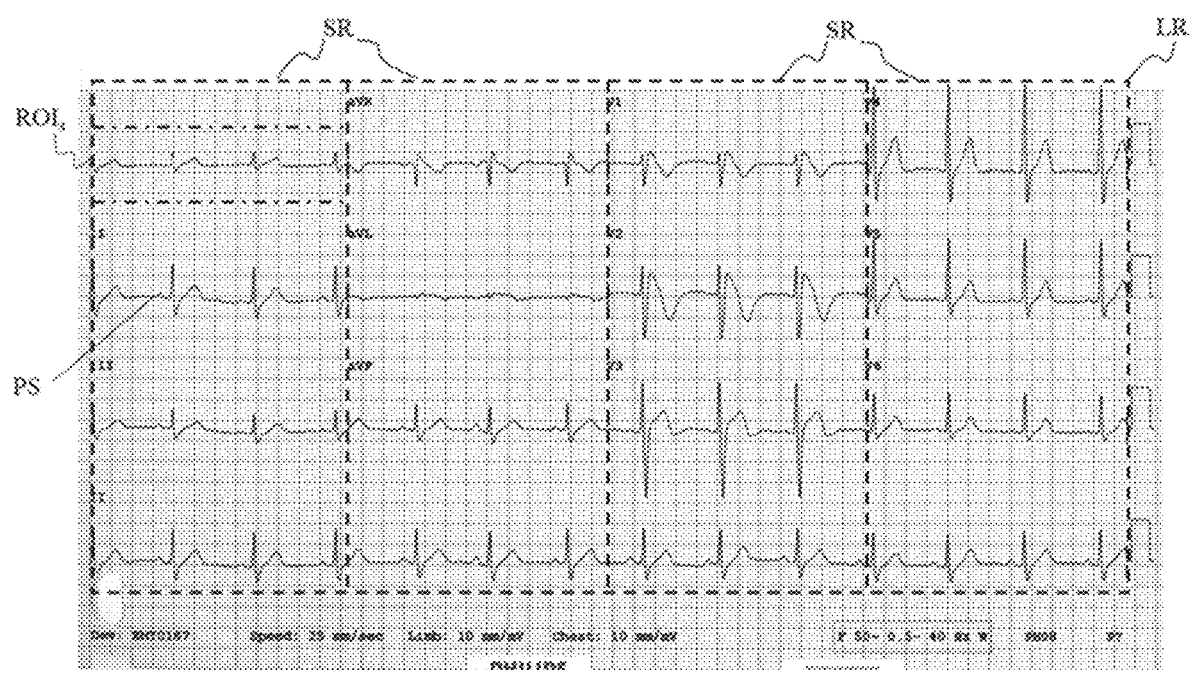
FIG. 6 is an example of a selection of at least one region of interest inside one of the identified sub-regions for an electrocardiogram representation having 3 rows, 4 columns and 1 rhythm lead.

Referring again to FIG. 2, each of the detected sub-regions may be segmented SEG at step 23. As is shown in FIG. 3, a flow chart of a more detailed view of step 23 is shown. Specifically, step 23 may involve sub-step 34 where at least one region of interest $ROI_s$ may be segmented via segmentation neural network $NN_2$ 27. The at least one region of interest $ROI_s$ may include, for example, at least a portion of the physiological signal PS, as shown in FIG. 6.

Segmentation neural network $NN_2$ 27 may be called segmentation neural network or second neural network interchangeably. Using segmentation neural network $NN_2$ 27 for Segmenting SEG, the input of segmentation neural network $NN_2$ 27 may be an image, for example, the image of one of the detected sub-region SR. The image may have dimensions (m×n, 1) or (m×n, 3), wherein m and n ranges from about 28 to about 2000 pixels, for example.

As is shown in FIG. 2, segmentation neural network $NN_2$ 27 may be configured to output information corresponding to at least one region of interest $ROI_s$. For example, step 23 may further include sub-step 35 of FIG. 3, where segmentation neural network $NN_2$ 27 may generate and thus the output of segmentation neural network $NN_2$ 27 may include at least (1) a dimension $d_r$ and a position $x_r$ of the at least one region of interest $ROI_s$ included in the image and (2) a probability $p_r$ of the presence of a portion of the physiological signal PS in the at least one region of interest $ROI_s$. The output may be presented as the following vector with three coefficients $y_{output} = [d_r, x_r, p_r]$.

As is shown in FIG. 2, the output of segmentation neural network $NN_2$ 27 may be used to define an input for extraction neural network $NN_3$ 28. In one example, the region of interest $ROI_s$ is defined by a rectangular boundary box, and the dimensions and the position of the region of interest $ROI_s$ are expressed by the coordinates of the center $[x_c; y_c]$ and the height $h_b$ of the rectangular boundary box. In this example, the output is $y_{output} = [h_b, (x_r; y_r), p_r]$.

Segmentation neural network $NN_2$ 27 may be a convolutional neural network. Segmentation neural network $NN_2$ 27 also may include multiple hidden layers such as convolutional layers, pooling layers, fully connected layers and normalization layers.

Segmentation neural network $NN_2$ 27 may include at least one convolutional layer with f filters of size (l×t) and stride of (d×g), where the number of filters f is inclusively between 1 and 2048, the filter size parameters l and t are inclusively between 1 and 25, and the stride parameters d and g are inclusively between 1 and 10. The advantage of using convolutional layers over fully connected layers is that convolutional layers allows reduction of the number of parameters to be trained.

Segmentation neural network $NN_2$ 27 may include a pooling layer, which produces a tensor of dimension (n×m×h), after the at least one convolutional layer. In one example, the pooling layer is a max pooling layer.

Alternatively, using multiple dense layers, segmentation neural network $NN_2$ 27 may further include at least a convolutional layer with f filters of size (l×t) and stride of (d×g), where the number of filters f is inclusively between 1 and 2048, the filter size parameters l and t are inclusively between 1 and 25, and the stride parameters d and g are inclusively between 1 and 10. Said convolutional layer may be followed by at least a pooling layer and at least one dense layer. The successive layers of segmentation neural network $NN_2$ 27 may be configured to produce at least an output of dimensions $(O_1, O_2)$, where this inclusively between 1 and 20 and $O_2$ is inclusively between 2 and 10.

Following a "fully convolutional" approach, segmentation neural network $NN_2$ 27 may further include at least two convolutional layers with f filters of size (l×t) and stride of (d×g), where the number of filters f is inclusively between 1 and 2048, the filter size parameters l and t are inclusively between 1 and 25, and the stride parameters d and g are inclusively between 1 and 10. This embodiment may produce at least an output of dimensions $(O_1, O_2)$, where this inclusively between 1 and 20 and $O_2$ is inclusively between 2 and 10.

This "fully convolutional" approach does not group all information in one output vector as in the "fully connected approach". The reduction of the number of parameters obtained with this approach has the advantage of reducing the computational cost and consequently improve performances.

In FIG. 8, segmentation neural network $NN_2$ 27 is configured to receive as input one image of dimensions inclusively between (200×200, 3) and (600×600, 3) and to produce as output the candidate regions of interest $ROI_s$ $y_{output} = [h_i, c_i, p_i]$, defined by 3 parameters: a probability $p_i$ of the presence of a real segment of ECG in the $i^{th}$ region of interest $ROI_s$ which may be $p_i \in [0,1]$; a centering variable defined as follows:

$$c_i = \frac{c_{signal} - c_{i,default}}{h_{default}}$$

where $c_{signal}$ is the center of the signal segment comprised in the region of interest $ROI_s$, $c_{i,default}$ is the center of the $i^{th}$ regions of interest $ROI_s$ defined by default, and $h_{default}$ is the height of the image divided by the number of candidate region of interest $ROI_s$; an a height variable defined as $$h_i = \frac{a_{signal}}{H}$$

where $a_{signal}$ is the maximal amplitude of the segment of signal comprised in the $i^{th}$ region of interest $ROI_s$ and H is the total height of the input image.

Referring again to FIG. 8, in the example shown the number of candidate region of interest $ROI_s$ is 16. Therefore, segmentation neural network $NN_2$ 27 involves a first convolutional layer with 64 filters of size (7×7) and stride (2×2), followed by 4 convolutional layers of filter size (3×3) with a number of filters respectively equal to 64, 128, 256 and 256.

In the "fully connected approach", segmentation neural network $NN_2$ 27 of the example in FIG. 8 may further include a convolutional layer with 512 filters of size (3×3) and stride (1×1) followed by a max pooling layer and two dense fully connected layers. This combination of layers provides an output of (16,3). Segmentation neural network $NN_2$ 27 may further include three convolutional layers, the first convolutional layer with 512 filters of size (3×3) and stride (1×1), the second convolutional layer with 128 filters of size (3×16) and stride (1×16) and the third layer with 3 filters of size (3×1) and stride (1×1). This succession of convolutional layers may also produce an output vector of (16,3).

Segmentation neural network $NN_2$ 27 may be trained with a supervised training. A loss function may be used in the training process of segmentation neural network $NN_2$ 27. The loss function may be a mean square error, mean absolute error and the like. The loss function may be defined as follows:

$$L(\hat{d}_r, \hat{x}_r, \hat{p}_r, d_r, x_r, p_r) = \lambda_{reg} L_{reg}(\hat{a}_r, \hat{x}_r, d_r, x_r, p_r) + \lambda_{prob} L_{prob}(\hat{p}_r, p_r)$$

where $\hat{d}_r$ is the dimensions of the at least one region of interest $ROI_s$ predicted by segmentation neural network $NN_2$ 27; $\hat{x}_r$ is the position of the at least one region of interest $ROI_s$ predicted by segmentation neural network $NN_2$ 27; and $\hat{p}_r$ is the probability of the presence of a portion of the physiological signal PS in the region of interest $ROI_s$ predicted by segmentation neural network $NN_2$ 27. The variables $d_r$, $x_r$ and $p_r$ represent the true dimensions, the true position and the true probability of the region of interest $ROI_s$, respectively. The variables $\lambda_{reg}$ and $\lambda_{prob}$ are hyperparameters to balance the influence of each loss value.

In one example, $L_{reg}(\hat{a}_r, \hat{x}_r, d_r, 1 x_r, p_r)$ is a loss function according to the formula:

$$L_{reg}(\hat{d}_r, \hat{x}_r, d_r, x_r, p_r) = \sum_{i=1}^{N} p^i \times (\hat{x}_r^i - x_r^i)^2 + p^i \times \left(\sqrt{\hat{d}_r^i} - \sqrt{d_r^i}\right)^2$$

and $L_{prob}(\hat{p}_r, p_r)$ is a binary cross-entropy according to the formula:

$$L_{prob}(\hat{p}_r, p_r) = \sum_{i=1}^{N} p^i \log(\hat{p}_r^i) + (1 - p_r^i)\log(1 - \hat{p}_r^i)$$

The segmentation neural network $NN_2$ 27 may be optimized using ADAGRAD, ADAM, ADAMAX or SGD (Stochastic Gradient Descent). Other optimization algorithm known by one skilled in the art may be used to implement said optimization step.

An ADADELTA optimizer may be used for segmentation neural network $NN_2$ 27 optimization. ADADELTA optimizer ensures a robust adaptive learning rate without tuning of a general learning rate (as opposed to Stochastic Gradient Descent) and showed to be a more stable learning curve than ADAGRAD. When using the ADADELTA optimizer, the images used as the training set for segmentation neural network $NN_2$ 27 are images of dimensions (m×n), wherein m and n ranges from 28 to 2000 pixels. These images may be represented in color or black and white depending on the color map used. Said training images involves a sub-region of an electroencephalographic and each training image is associated to the true number of region of interest $ROI_s$, the true dimensions, true position and the true probability of an ECG signal of each region of interest $ROI_s$ comprised in said sub-region SR.

As is shown in FIG. 2, after applying segmentation neural network $NN_2$ 27, extraction EXT may be performed at step 24 by applying extraction neural network $NN_3$ 28. As is shown in FIG. 3, a flow chart of a more detailed view of step 24 is shown. Specifically, step 24 may involve sub-step 36, where a probability map for each region of interest $ROI_s$ may be generated. Further, step 24 may further involve sub-step 37 where the coordinates $COOR_s$ representing the physiological signal PS may be extracted. Accordingly, extraction neural network $NN_3$ 28 may output the coordinates $COOR_s$ representing the physiological signal PS. In this disclosure, this neural network will be called extraction neural network or third neural network interchangeably.

Extraction neural $NN_3$ 28 architecture may be based on a VGGnet (Karen Simonyan and Andrew Zisserman. "*Very Deep Convolutional Networks for Large-Scale Image Recognition.*" arXiv:1409.1556 [cs], September 2014). Said VGGnet network architecture is characterized by its simplicity, using only 3×3 convolutional layers stacked on top of each other in increasing depth. In this kind of architecture, the reduction of volume size is handled by max pooling layers. Two fully-connected layers, each with 4,096 nodes may then be followed by a softmax classifier layer.

The input of extraction neural network $NN_3$ 28 may be an image of dimension (m×n, 1) or (m×n, 3), where m and n ranges from 28 to 2000 pixels, and is an image having at least a segment of a physiological signal PS of a subject. As is shown in FIG. 2, the output of segmentation neural network $NN_2$ 27 may be used as input for extraction neural network $NN_3$ 28. The output of segmentation neural network $NN_2$ 27 ($d_r$, $x_r$, $p_r$) may be used to extract the image of the at least one region of interest $ROI_s$ from the image inputted in segmentation neural network $NN_2$ 27. The segmentation of the image corresponding to the at least one region of interest $ROI_s$ identified by segmentation neural network $NN_2$ 27 may be obtained with a one region pooling layer.

Extraction neural network $NN_3$ 28 may be configured to output coordinates $COOR_s$ representing the physiological signal PS as a unidimensional vector of dimension v inclusively between 28 and 2000, for example.

Extraction neural network $NN_3$ 28 may be a convolutional neural network and/or may involve multiple hidden layers such as convolutional layers, pooling layers, fully connected layers and normalization layers. Extraction neural network $NN_3$ 28 may include at least a convolutional layer followed by at least one pooling layer and at least a transpose convolutional layer.

In one example, extraction neural network $NN_3$ 28 may include a number of weight layers inclusively between 11 and 19, grouped into at least 4 convolutional blocks, each of said weight layers using a filter size of 3×3. The convolution blocks of extraction neural network $NN_3$ 28 may be separated by max pooling layers. The max-pooling may be performed over a 2×2 pixels window, with a stride of 2. The last convolutional block may be followed by a max pooling layer and at least one fully-connected layer.

Figure 10:
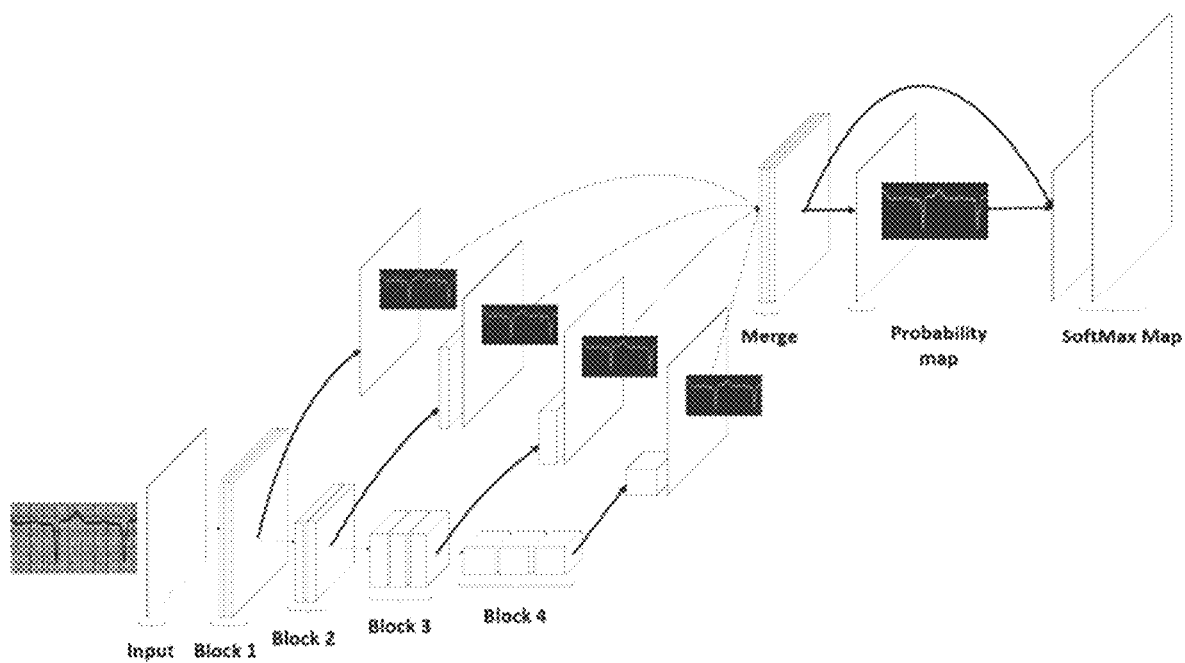
FIG. 10 is an exemplary illustration of architecture of the extraction neural network, where the last layer is a softmax layer.

Extraction neural network $NN_3$ 28 may not include fully-connected layers. The last layer of extraction neural network $NN_3$ 28 may be a softmax layer, as shown in FIG. 10. And all hidden layers may be equipped with the rectification non-linearity (ReLU) (Krizhevsky, Sutskever, I., and Hinton, G. E. "*ImageNet classification with deep convolutional neural networks.*" In NIPS, pp. 1106-1114, 2012).

Extraction neural network $NN_3$ 28 is composed of 4 convolutional blocks, for example, each followed by a max pooling layer. The implementation of fewer than 5 convolutional blocks allows significant reduction of the computation cost while keeping dimensions of the feature map that are relevant for a pixel-precise prediction. In this example, the extraction neural network $NN_3$ 28 is configured to merge information from the first layers, in order to keep low-level details of the image, and the last layers, in order to keep object-level information, allowing a pixel-precise (low-level) feature map in which only relevant objects are kept (high-level: e.g., removing the background). In this example, the four convolutional blocks are followed by a (3×3) convolutional layer and a column wise max pooling layer, producing therefore the output vector.

Extraction neural network $NN_3$ 28 may be trained in a supervised training. For example, a loss function may be used. The loss function may be a mean square error, mean square logarithmic error, mean absolute error, mean absolute percentage error, L2 or one of the like. A L2 regularizing factor for the value of the network weight of $10^{-3}$ may be added to obtain better generalization.

Extraction neural network $NN_3$ 28 may be optimized using a gradient descent algorithm. The optimization may be performed using ADAGRAD, ADAM, ADAMAX or SGD (Stochastic Gradient Descent). Other optimization algorithm known by one skilled in the art may be used to implement said optimization step.

The images used as training set for extraction neural network $NN_3$ 28 may be images of dimensions (m×n), wherein m and n ranges from 28 to 2000 pixels, for example, including at least a segment of the physiological signal PS. Each of said training images are associated to a vector having the true coordinates of the physiological signal PS in the image.

Extraction neural network $NN_3$ 28 may be trained with a batch gradient descent. Batch gradient descent is a variation of the gradient descent algorithm that calculates the error for each example in the training dataset, but only updates the model after all training examples have been evaluated.

Extraction neural network NN₃ 28 may be configured to produce a first intermediate output. Said first intermediate output involves generation of a probability map which, according to one embodiment, is used to obtain a final output consisting in the coordinates $COOR_{ex}$ associated to the physiological signal PS.

Alternatively, extraction neural network NN₃ 28 may be an image of dimension (m×n, 1) or (m×n, 3), wherein m and n ranges from 28 to 2000 pixels, for example, and is an image including at least a segment of a physiological signal PS of a subject. The output of segmentation neural network NN₂ 27 may be used as input for extraction neural network NN₃ 28. The output of segmentation neural network NN₂ 27 ($d_r$, $x_r$, $p_r$) may be used to extract the image of the at least one region of interest $ROI_s$ from the image inputted in segmentation neural network NN₂ 27. The segmentation of the image corresponding to the at least one region of interest $ROI_s$ identified by segmentation neural network NN₂ 27 may be obtained with a one region pooling layer.

In this example, extraction neural NN₃ 28 includes a number of weight layers inclusively between 11 and 19, grouped into at least 4 convolutional blocks, each of said weight layers using a filter size of 3×3. The convolutional blocks of extraction neural network NN₃ 28 may be separated by max pooling layers.

An intermediate prediction using a convolutional layer or a combination of a convolutional layer and a convolutional transposed layer may be extracted from each of the convolutional blocks. The last convolutional block may be followed by a merging operation concatenating at least two of the intermediate prediction into a new intermediate prediction of the probability map. Said merging operation may be followed by at least one convolutional layer. An operation may be performed to select at least one of the intermediate prediction or a concatenation of at least two of the intermediate prediction. Said selection may be followed by at least a (3×3) convolutional layer and/or at least on transposed convolutional layer. These last convolutional layers may be followed by a softmax layer column-wise to outline the location of the signal at each column and obtain the intermediate output of the probability map. The final step may include performing an arg max operation on the column of the probability map in order to extract the coordinates of the $COOR_{ex}$ of the physiological signal segment PS comprised in the region of interest $ROI_s$.

Figure 9:
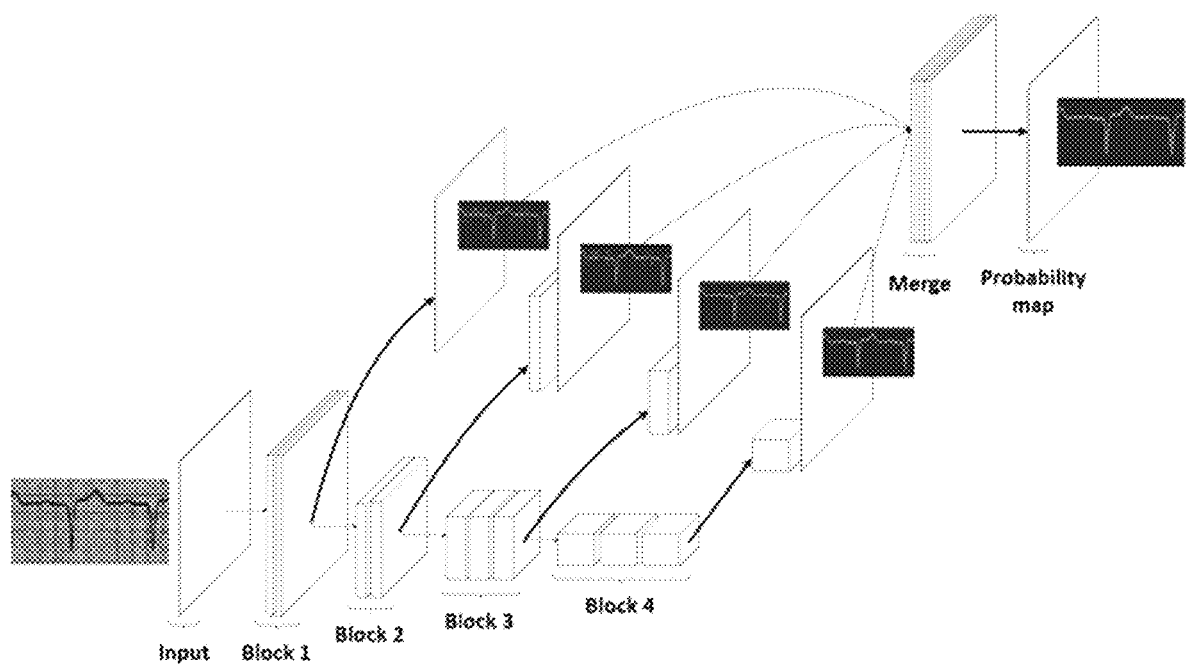
FIG. 9 is an exemplary illustration of architecture of the extraction neural network.

Referring now to FIG. 9, extraction neural network NN₃ 28 may be configured to receive as input a color image of dimension inclusively between (200×200,3) and (600×600, 3) having a segment of physiological signal PS. As is shown in FIG. 9, extraction neural network NN₃ 28 includes a first convolutional block having two (3×3) convolutional layers with 64 filters followed by a first maxpooling layer. A first prediction image (wxh,1) is obtained using a convolutional layer after the first convolutional block. The first maxpooling is followed by a second convolutional block having two (3×3) convolutional layers of 128 filters and a second maxpooling layer. A second prediction image (wxh,1) is obtained using a convolutional layer and a transposed convolutional layer which multiples the dimension of the prediction image by a factor of two. The second max pooling is followed by a third convolutional block including three (3×3) convolutional layers having 256 filters and a third maxpooling layer. A third prediction image (wxh,1) is obtained using a convolutional layer and a transposed convolutional layer which multiples the dimension of the prediction image by a factor of 4. The third maxpooling is followed by a block of four (3×3) convolutional layers having 512 filters and a convolutional transposed layer producing a fourth prediction image (wxh,1). In this example the first, second, third and fourth prediction images are concatenated obtaining a feature map of dimensions (wxh,4). This step is followed by two (3×3) convolutional layers producing a fifth prediction image.

In this example the five prediction images are merged on the third dimension and this operation is followed by a (3×3) convolutional layer and a transposed convolutional layer to obtain probability maps of twice the size. A softmax classifier layer is then used to enhance the maximum value in the probability map. Finally, an arg max operation on each column of the probability may be performed in order to extract the coordinates on the abscissa of the physiological signal PS.

Referring again to FIG. 2, after applying the extraction neural network NN₃ 28 in order to extract the coordinates of the $COOR_{ex}$ of the physiological signal segment PS comprised in the region of interest $ROI_s$, the extracted coordinates $COOR_{ex}$ may be registered REG at step 25 of on a transitory or not-transitory computer readable storage medium.

The three neural networks, division neural network NN₁ 26, segmentation neural network NN₂ 27, and extraction neural network NN₃ 28, may be separate and unique neural networks or may be one neural network having the features and functionality described herein with respect to each.

The methods of the present disclosure may be implemented using machine learning algorithms other than Neural Networks such as Super Vector Machine, k Nearest Neighbor or Extreme Learning Model and the like, and all possible combinations thereof and with Neural Networks.

Division neural network NN₁ 26, segmentation neural network NN₂ 27 and extraction neural network NN₃ 28 may be trained separately or alternatively, at the same time.

In one example, division neural network NN₁ 26, segmentation neural network NN₂ 27 and extraction neural network NN₃ 28 are defined and trained using Keras library with Tensorflow backend (Francois Chollet et al. Keras. https://github.com/keras-team/keras, 2015).

The operations described herein with respect to FIG. 2 may be implemented by hardware components. Examples of hardware components include controllers, sensors, generators, drivers, memories, comparators, arithmetic logic units, adders, subtractors, multipliers, dividers, integrators, neural networks, signal separators, calculators, extractors, determiners, and any other electronic components known to one of ordinary skill in the art. In one example, the hardware components are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIG. 2. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art may readily write the instructions or software based on the block diagrams and the flow charts illustrated in the drawings and the corresponding descriptions in the specification, which disclose algorithms for performing the operations performed by the hardware components and the methods as described above.

Another aspect of the present disclosure relates to computer program product for the conversion of a digitized curve representing a physiological signal PS of a subject. The computer program product having instructions which, when the program is executed by a computer, cause the computer to automatically carry out the steps of the method according to any one of the embodiments described here above. The execution of the computer program is initiated by a command, which may be given by a user through an interactive interface or by a second computer program. The instruction comprised in the computer program are such to allow the automatic execution of all the consecutive steps of the method according to the embodiment of the present description from the initial step of reception of the digitized image $I_d$ to the final step of registering the extracted coordinates $COOR_{ex}$.

Yet another aspect of the present disclosure relates to a computer-readable storage medium having instructions which, when the program is executed by a computer, cause the computer to carry out the steps of the computer-implemented method according to anyone of the embodiments described here above. According to one embodiment, the computer-readable storage medium is a non-transitory computer-readable storage medium.

Computer programs implementing the method of the present embodiments may commonly be distributed to users on a distribution computer-readable storage medium such as, but not limited to, an SD card, an external storage device, a microchip, a flash memory device and a portable hard drive. From the distribution medium, the computer programs may be copied to a hard disk or a similar intermediate storage medium. The computer programs may be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer may execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While various embodiments have been described and illustrated, the detailed description is not to be construed as being limited hereto. Various modifications may be made to the embodiments by those skilled in the art without departing from the true spirit and scope of the disclosure as defined by the claims.

What is claimed is:

1. A method for digital conversion of a printed representation of a physiological signal of a subject, the method comprising:
   receiving a digitized image of the printed representation of the physiological signal of the subject;
   detecting, via a first neural network, a layout region of the digitized image and at least one sub-region dividing the layout region;
   detecting, via a second neural network, at least one region of interest inside one of the identified sub-regions comprising a portion of the physiological signal; and
   extracting, via a third neural network, coordinates representing the physiological signal for each of the at least one region of interest.

2. The method of claim 1, wherein the physiological signal includes an electrocardiogram.

3. The method of claim 1, further comprising registering the coordinates representing the physiological signal on a computer readable storage medium.

4. The method of claim 1, wherein the first neural network receives as an input the digitized image and generates as an output one or more of (i) at least one characteristic dimension, (ii) a position of the layout region, and (iii) the number of sub-regions.

5. The method of claim 1, wherein the second neural network receives as an input an image of one of the at least one sub-region and generates as an output one or more of (i) a dimension and a position of the at least one region of interest, and (ii) a probability of the presence of a portion of the physiological signal in the at least one region of interest.

6. The method of claim 1, wherein the third neural network receives as an input one or more of (i) a dimension and a position of the at least one region of interest, and (ii) a probability of the presence of a portion of the physiological signal in the at least one region of interest and generates as an output the coordinates representing the physiological signal.

7. The method of claim 6, wherein the third neural network generates as an output a probability map used to obtain the coordinates representing the physiological signal.

8. The method of claim 1, wherein the first neural network comprises at least two hidden layers, the second neural network comprises at least two hidden layers, and the third neural network comprises at least two hidden layers.

9. The method of claim 1, wherein the second neural network includes a convolutional neural network and comprises a pooling layer.

10. The method of claim 1, wherein the third neural network is a convolutional neural network comprising at least one convolutional layer followed by at least one pooling layer and at least one transpose convolutional layer.

11. A method for digital conversion of a printed representation of a physiological signal of a subject, the method comprising:
    receiving a digitized image of a printed representation of a physiological signal;
    detecting a layout region;
    dividing the layout region into at least one sub-region;
    generating at least one characteristic dimension of the layout region, a position of the layout region, and a number sub-regions;
    for each of the at least one sub-regions, segmenting, via a segmentation neural network, at least one region of interest comprising a portion of the physiological signal, wherein an input of the segmentation neural network is an image of the at least one sub-region and an output comprises a dimensions and a position of the at least one region of interest, and a probability of the presence of a portion of the physiological signal in the at least one region of interest; and
    for each region of interest, extracting, via an extraction neural network, coordinates representing the physiological signal.

12. The method of claim 11, wherein the detection of the layout region and of the at least one sub-region is performed using a division neural network.

13. The method of claim 12, wherein the division neural network comprises at least two hidden layers.

14. The method of claim 12, wherein the division neural network comprises a convolutional neural network comprising at least two parallel dense layers, wherein a first parallel dense layer corresponds to the output of the characteristic dimension of the layout region and a second parallel dense layer corresponds to the number of sub-regions.

15. The method of claim 11, wherein the segmentation neural network comprises at least two hidden layers and the extraction neural network comprises at least two hidden layers.

16. The method of claim 11, wherein the output of the segmentation neural network is an input of the extraction neural network.

17. The method of claim 11, further comprising, for each region of interest, generating, via an extraction neural network, a probability map from which the coordinates representing the physiological signal is extracted.

18. The method of claim 11, wherein the segmentation neural network includes a convolutional neural network and comprises a pooling layer.

19. The method of claim 11, wherein the extraction neural network is a convolutional neural network comprising at least one convolutional layer followed by at least one pooling layer and at least one transpose convolutional layer.

20. A system for conversion of a printed curve representing a physiological signal of a subject into a digitized curve, the system comprising instructions stored on at least one processor, the instructions configured to, when executed, cause the at least one processor to:
    receive a digitized image of a printed curve representing the physiological signal of the subject;
    detect, via a first neural network, a layout region of the digitized image and at least one sub-region dividing the layout region;
    detect, via a second neural network, at least one region of interest comprising a portion of the physiological signal inside one of the at least one sub-region; and
    extract, via a third neural network, coordinates representing the physiological signal for each of the at least one region of interest.

* * * * *